(12) United States Patent
Kong

(10) Patent No.: US 6,619,284 B2
(45) Date of Patent: Sep. 16, 2003

(54) HAND-HELD COMPRESSOR NEBULIZER

(76) Inventor: Geok Weng Kong, Room 406, 4th Fl, Winsom Industrial Bldg, 588-592 Castle Peak Road, Cheung Sha Wan, Kowloon (HK)

(*) Notice: Subject to any disclaimer, the term of this patent is extended or adjusted under 35 U.S.C. 154(b) by 232 days.

(21) Appl. No.: 09/847,441

(22) Filed: May 3, 2001

(65) Prior Publication Data

US 2001/0037807 A1 Nov. 8, 2001

(30) Foreign Application Priority Data

May 4, 2000 (HK) .......................................... 00102694

(51) Int. Cl.[7] .............................................. A61M 11/00
(52) U.S. Cl. ............................ 128/200.21; 128/200.18; 128/200.16; 128/200.11; 128/200.13; 128/200.14; 239/338
(58) Field of Search ................ 128/200.21, 200.18, 128/200.16, 200.11, 200.13, 200.14; 239/338, 370, 340

(56) References Cited

U.S. PATENT DOCUMENTS

| | | | |
|---|---|---|---|
| 4,007,238 A | | 2/1977 | Glenn |
| 4,588,129 A | * | 5/1986 | Shanks ....................... 239/338 |
| 4,746,067 A | * | 5/1988 | Svoboda ..................... 239/338 |
| 4,792,097 A | | 12/1988 | Kremer, Jr. et al. |
| 5,054,477 A | | 10/1991 | Terada et al. |
| 5,203,506 A | | 4/1993 | Gross et al. |
| 5,235,969 A | | 8/1993 | Bellm |
| 5,653,227 A | * | 8/1997 | Barnes et al. ........... 128/203.12 |
| RE36,070 E | * | 2/1999 | Ballini et al. ............ 128/200.14 |
| 5,893,515 A | | 4/1999 | Hahn et al. |
| 6,129,080 A | * | 10/2000 | Pitcher et al. ........... 128/200.21 |
| 6,237,589 B1 | * | 5/2001 | Denyer et al. ........... 128/200.21 |
| 6,513,727 B1 | * | 2/2003 | Jaser et al. ..................... 239/71 |

FOREIGN PATENT DOCUMENTS

| | | |
|---|---|---|
| WO | WO 98/07464 A1 | 2/1998 |
| WO | WO 99/11310 A1 | 3/1999 |

* cited by examiner

*Primary Examiner*—Weilun Lo
*Assistant Examiner*—Darwin P. Erezo
(74) *Attorney, Agent, or Firm*—Leydig, Voit & Mayer, Ltd.

(57) ABSTRACT

A hand-held compressor nebulizer suitable for vaporizing liquid medication, comprising a casing and a motor-driven air pump. The nebulizer includes a liquid medication supply unit and a vaporizing unit. The vaporizing unit comprises upper and lower vaporizing chambers, the lower chamber including a reservoir for liquid medication from the liquid medication supply unit. The vaporizing unit includes a hollow conical member located within the lower chamber and defining an internal conical passage having a relatively smaller upper end and a relatively larger lower end, the lower end being in communication with the air pump for receiving an upward airflow produced by the air pump. The airflow increases in speed in the upward direction and creates a negative pressure upon exit from the upper end of the conical passage. The vaporizing unit further includes a vaporizing jacket having a tapered interior and disposed around the conical member to form a narrow gap with the conical member. The gap has an upper end in the vicinity of the upper end of the conical passage and a lower end in communication with the reservoir such that the negative pressure can cause, by way of suction, liquid medication in the reservoir to move upwards along the gap and subsequently be vaporized by the airflow upon exit from the upper end of the gap.

18 Claims, 3 Drawing Sheets

HAND-HELD COMPRESSOR NEBULIZER

The present invention relates to a vaporizing device and, particularly but not exclusively, to a vaporizing device for vaporizing liquid medication.

BACKGROUND OF THE INVENTION

One of the known nebulizers extensively used is ultrasonic nebulizer, which utilizes ultrasonic vibration waves to atomize or vaporize liquid. One disadvantage of ultrasonic nebulizers is that the mist produced is usually about 1–10 micron in size, which is not sufficiently fine for the respiratory tract of a patient to absorb medication. In addition, by reason of the complicate mechanism, large physical size and high power consumption, typical ultrasonic nebulizers are often only suitable for hospital and household use, and they are inconvenient to carry in transit or during travelling for use anytime and/or anywhere as needed.

The invention seeks to mitigate or at least alleviate such problems by providing a hand-held compressor nebulizer, which is lightweight, compact and convenient to carry and can be used at any moment, with a relatively smaller vaporized particle size.

SUMMARY OF THE INVENTION

According to the invention, there is provided a hand-held compressor nebulizer suitable for vaporizing liquid medication, comprising a casing, an air pump located within the casing an electric motor located within the casing for driving the air pump, and an electrical switch for controlling the operation of the motor. The nebulizer includes a liquid medication supply unit for supplying liquid medication and a vaporizing unit, both provided on the upper part of the casing. The vaporizing unit comprises an upper vaporizing chamber and a lower vaporizing chamber, the lower chamber including a reservoir into which the liquid medication supply unit is to supply liquid medication. The vaporizing unit includes a hollow conical member located within the lower vaporizing chamber and defining an internal conical passage having a relatively smaller upper end and a relatively larger lower end, the lower end being in communication with the air pump for receiving an upward airflow produced by the air pump. The airflow increases in speed in the upward direction and creates a negative pressure upon exit from the upper end of the conical passage. The vaporizing unit further includes a vaporizing jacket having a tapered interior and disposed around the conical member to form a narrow gap between the jacket and the conical member. The gap has an upper end in the vicinity of the upper end of the conical passage and a lower end in communication with the reservoir, such that the negative pressure can cause, by way of suction, liquid medication in the reservoir to move upwards along the gap and subsequently be vaporized by the airflow upon exit from the upper end of the gap.

Preferably, the upper vaporizing chamber is formed within the vaporizing unit and the lower vaporizing chamber is defined by a member extending across an uppermost end of the casing.

It is preferred that the liquid medication supply unit comprises a holder for holding a liquid medication box closed by a sealing tape, and a slider for piercing open said tape to allow liquid medication in said box to flow out into the reservoir.

It is further preferred that the medication box holder is located on the upper vaporizing chamber, and that the slider and said medication box are arranged on opposite sides within the holder, which slider is resiliently biased away from said medication box by means of a spring and is movable against the action of the spring to pierce through said tape.

Preferably, the vaporizing unit includes a lid having an air inlet above the upper vaporizing chamber to enable communication of the upper vaporizing chamber with the ambiant atmosphere, and an adjuster provided immediately below the lid for movement to adjust the opening size of the air inlet.

Preferably, the air pump is one of a valve-type pump and a plunger-type pump.

Preferably, the motor has a power rating of substantially 18 watt.

Preferably, the sealing tape is made of one of paper and tin foil.

Advantageously, the nebulizer may have a maximum size of 7 cm×6 cm×23 cm, and a maximum weight of 750 grams.

In a preferred embodiment, the upper and lower ends of the conical passage defined by the conical member are substantially 0.7 mm and 3.0 mm in diameter respectively.

It is preferred that the gap formed between the jacket and the conical member is conical and has a gap width of substantially 0.5 mm.

BRIEF DESCRIPTION OF DRAWINGS

The invention will now be more particularly described, by way of example only, with reference to the accompanying drawings, in which.

DETAILED DESCRIPTION OF PREFERRED EMBODIMENT

Figure 1:
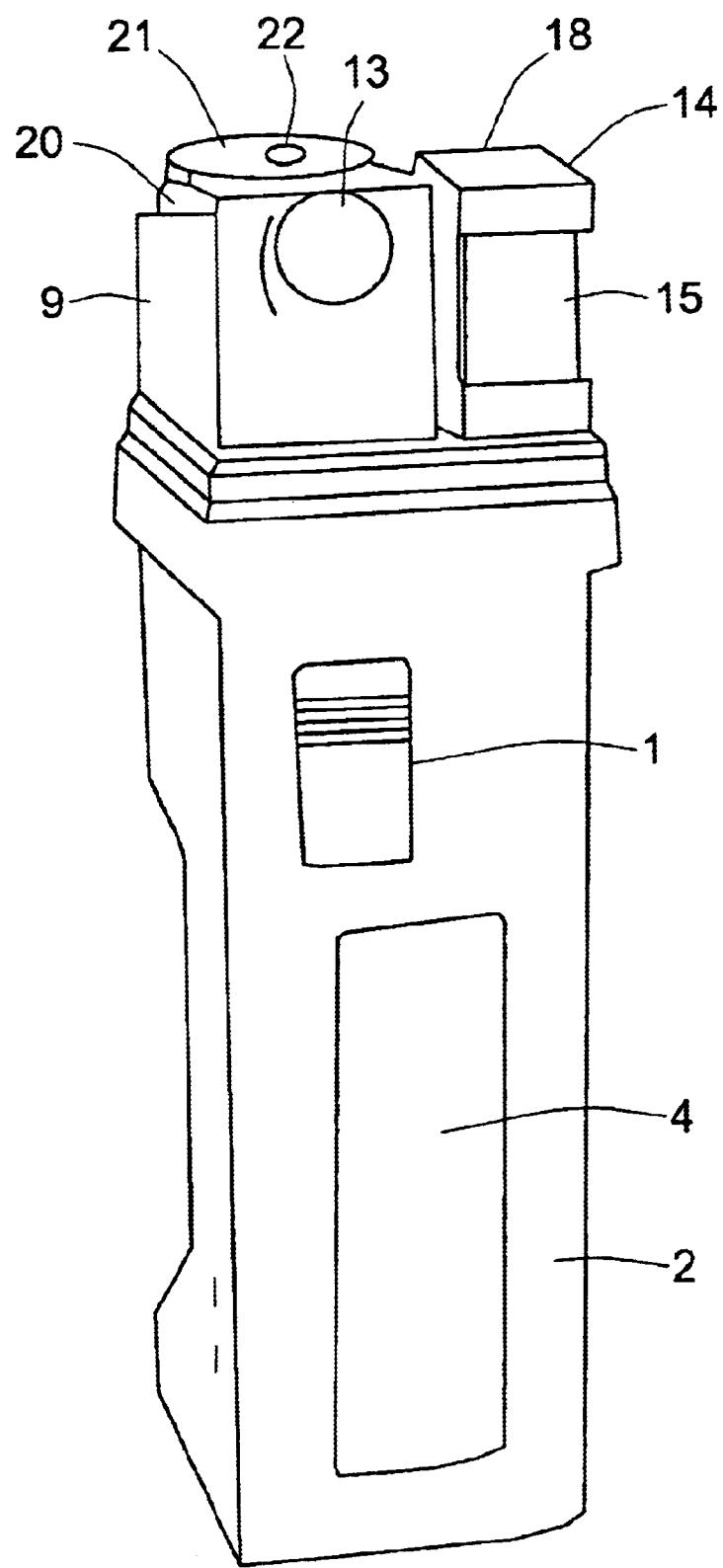
FIG. 1 is a perspective view of an embodiment of a hand-held compressor nebulizer in accordance with the invention.
Figure 2:
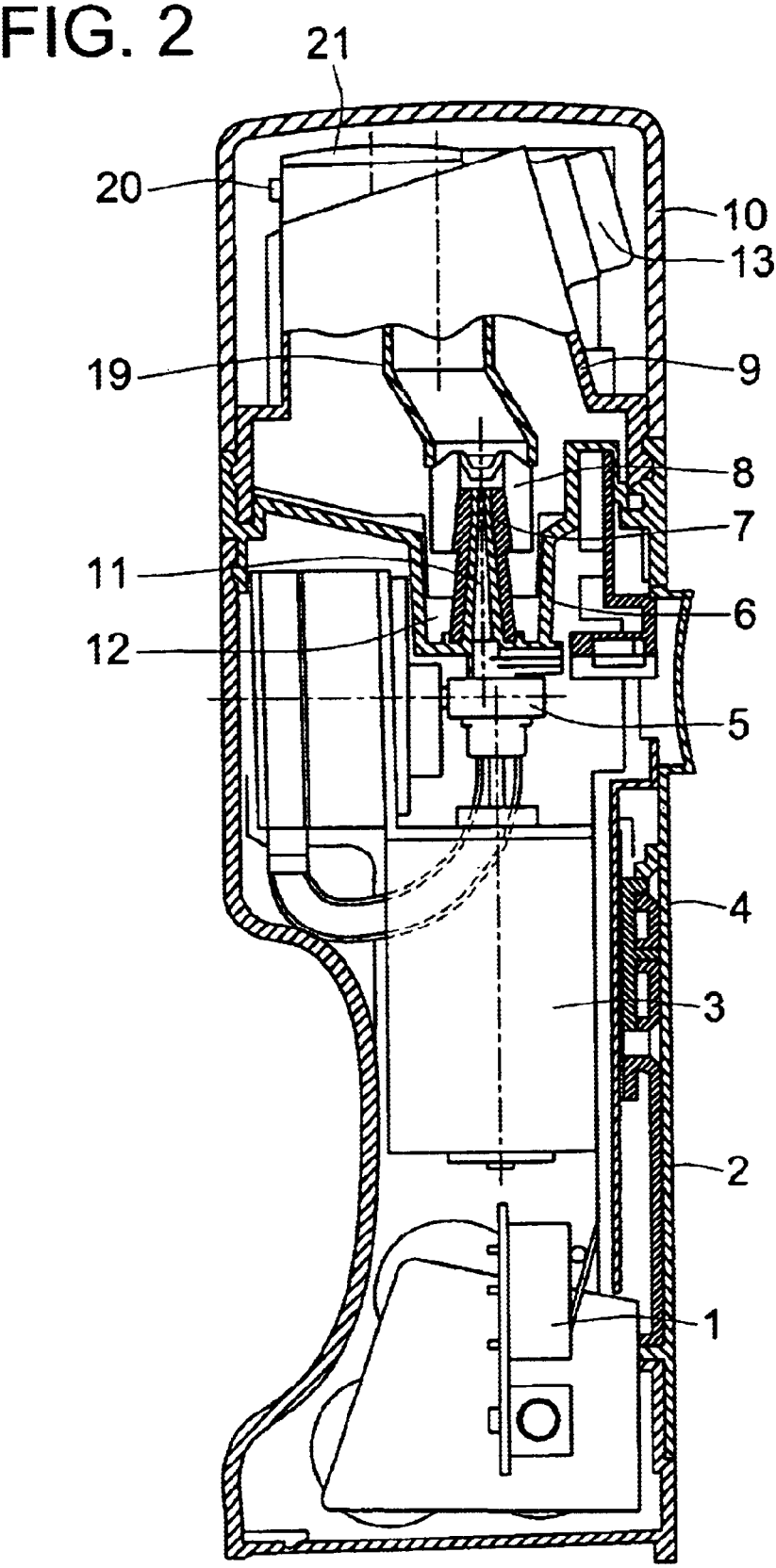
FIG. 2 is a cross-sectional side view of the nebulizer of FIG. 1.
Figure 3:
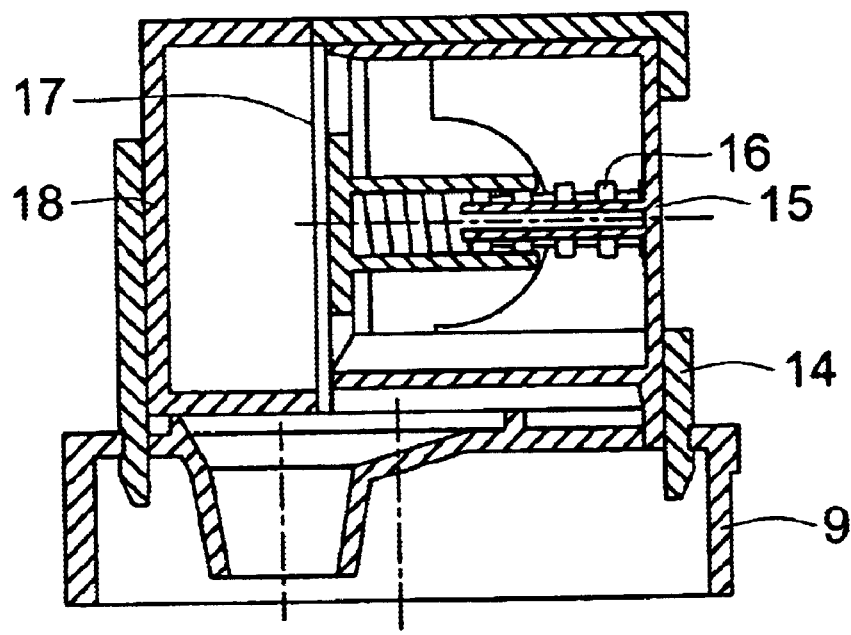
FIG. 3 is a cross-sectional side view of a first upper part of the nebulizer of FIG. 1.
Figure 4:
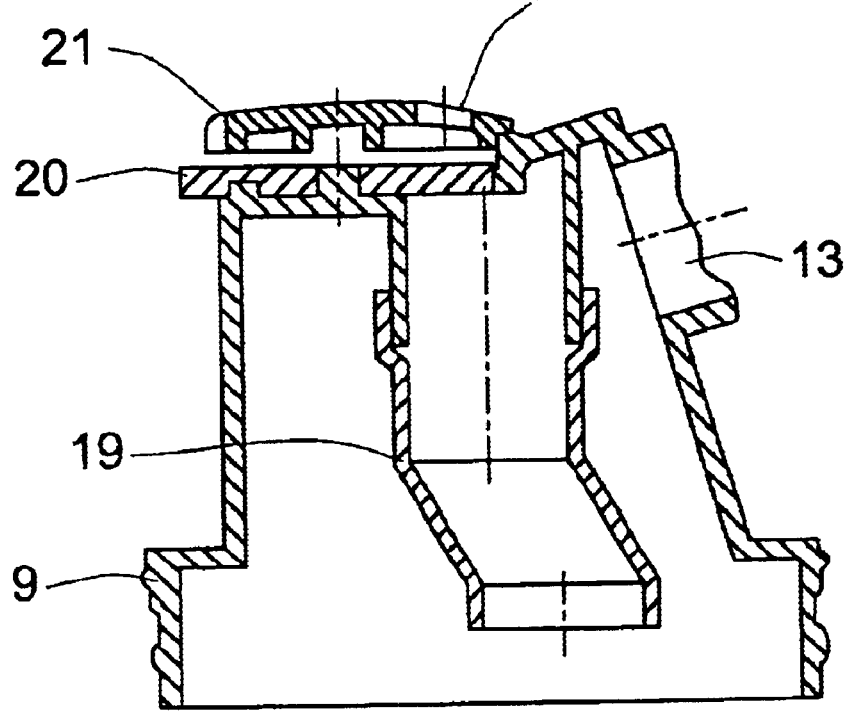
FIG. 4 is a cross-sectional side view of a second upper part of the nebulizer of FIG. 1.

Referring initially to FIG. 1 of the drawings, there is shown a hand-held compressor nebulizer embodying the invention, which nebulizer has a body that can be divided into three parts, i.e. a vaporizing unit at the upper left corner, a liquid medication supply unit at the upper right corner and a pneumatic unit as the middle lower section.

The vaporizing unit comprises an upper vaporizing chamber (9) which has a shell structure and is provided, on its front side, with a vaporized air outlet (13) having an opening that is inclined slightly upwards. The vaporizing unit includes a lower vaporizing chamber (6) defined by a member extending across the uppermost end of the casing (2), which is to be connected with the upper vaporizing chamber (9) to form a complete vaporizing chamber (9 and 6). The upper chamber (9) includes an upper lid (21) formed with an air inlet (22), and a turnable disc (20) located immediately below the lid (21) for adjusting the opening size of the air inlet (22) to control the amount of intake air and in turn the concentration of vaporized medication dispensed.

The liquid medication supply unit comprises a medication box holder (14), a liquid medication box (18) and a slider (15). The pneumatic unit comprises a casing (2), an electrical switch (1) and a panel (4).

The subject nebulizer has a compact structure and a small configuration and is easy to carry. It may include an upper cap (10) for covering and protecting the vaporizing unit and the liquid medication supply unit. The pneumatic unit is made narrower along its central mid-length to facilitate gripping by one hand.

Reference is also made to FIG. 2, which is a cross-sectional side view of the subject nebulizer, showing all of its components being contained within the casing (2) and the cap (10). The nebulizer includes an 18-watt electric motor (3) located centrally within the casing (2), a circuit board associated with the power switch (1) for controlling the operation of the motor (3), and an air pump (5) having an outlet nozzle and arranged to be driven by the motor (3). The air pump (5) may be a valve-type or plunger-type pump, having its outlet nozzle located immediately below the lower vaporizing chamber (6). The panel (4) is provided on the same side of the casing (2) as the vaporized air cutlet (13).

The lower vaporizing chamber (6) resembles a funnel, having an upper side connected with the upper vaporizing chamber (9), thereby forming a complete vaporizing chamber. More specifically, the upper peripheral edge of the lower chamber (6) is connected, on the lower side, to the casing (2) and, on the upper side, to the upper chamber (9) through annular engagement between a flange and a groove.

The lower vaporizing chamber (6) has a bottom wall that is formed integrally with a vertically depending slim pipe. The lower end of the pipe is aligned with and pressed against the nozzle of the air pump (5), such that air from the pump (5) may enter into the pipe and in turn the lower chamber (6). The underside of the lower chamber (6) includes integrally a horizontal slim pipe that has an inner end in communication with the vertical pipe and an open outer end, for supply of air.

A vertical slender hollow conical member or cone is located on the bottom wall of the lower vaporizing chamber (6), at a position aligned with the slim pipe. The cone defines an internal conical passage (11) for air, and its apex forms a nozzle.

The inner surface of the lower vaporizing chamber (6) around the cone is recessed and acts as a reservoir (12) for containing liquid medication received from the liquid medication box (18). The surface surrounding the periphery of the reservoir (12) is inclined downwards for guiding the liquid medication to flow into the reservoir (12).

A vaporizing jacket (7) including a vaporizing cap (8) is placed over the cone. The jacket (7) has a tapered interior or inner surface to form a narrow conical gap with the outer surface of the cone, along which gap liquid medication from the reservoir (12) is to travel upwards when subject to suction. The conical gap has a gap width of about 0.5 mm.

As shown in FIG. 3 showing the liquid medication supply unit in greater detail, the medication box holder (14) is a rectangular shell including a pair of downwardly projecting front and rear bottom hooks for insertion into respective holes of the top of the upper vaporizing charter (9). The hooks are chamfered on their outer sides for releasably connecting the holder (14) onto the upper chamber (9) through a snap-fit action. The liquid medication supply unit is detachable, for cleaning whenever necessary, by compressing the holder (14) to release the hooks from the holes.

The liquid medication box (18) is rectangular, including an open side that is initially sealed by means of a sealing tape (17) for containing liquid medication therein. The tape (17) may be of paper or tin foil. The medication box (18) is to be inserted into the rear part of the holder (14) for use, with the sealing tape (17) facing inwards.

The slider (15) is hollow rectangular and located within the front part of the holder (14), and is resiliently biased forwards by means of a compression spring (16). The slider (15) includes a pair of upper and lower rearwardly extending tooth-shaped prongs. Upon depression against the action of the spring (16), the slider (15) slides inwards carrying with it the prongs, which pierce through the sealing tape (17) to form two holes. Upon release, the slider (15) and its prongs are returned by the spring (16), and the holes allow liquid medication to flow out from the box (18) and run into the reservoir (12) of the lower vaporizing chamber (6).

In general, the liquid medication is supplied in a sealed manner within the box (18) for use as described above. Alternatively, suitable liquid medication may be poured into the reservoir (12), after the medication box holder (14) has been removed, whereupon an empty liquid medication box should be inserted into the holder (14) to prevent leakage.

Reference is also made to FIG.4, which shows the vaporizing unit in greater detail. As mentioned above, the lid (21) of the upper vaporizing chamber (9) has an air inlet (22). The disc (20), which is formed with a cut-out, is located immediately below the lid (21) to extend across a top opening of the upper chamber (9) for turning to adjust the size of the air inlet (22). The top opening of the upper chamber (9) acts as an orifice (about 8.0 mm in diameter) for aeration, integrally from the lower side of which an angled connecting pipe (19) extends downwards to reach and surround the vaporizing cap (8).

The size of the opening through the air inlet (22) of the lid (21) and the orifice of the upper vaporizing chamber (9) is adjustable by means of the turnable disc (20), via its cut-out, for controlling the amount of intake air and in turn the concentration of vaporized medication to be dispensed.

The operation of the subject hand-held compressor nebulizer will now be described. A power supply, which is provided by a rechargeable battery contained within the casing (2) of the nebulizer, is initially connected by means of the power switch (1) to turn on the electric motor (3). The motor (3) drives the air pump (5) to compress air and produce a high-speed airflow upwards through the conical passage defined by the cone in the lower vaporizing chamber (6). As the conical passage has a relatively smaller upper end (about 0.7 mm in diameter) and a relatively larger lower end (about 3.0 mm in diameter), the speed of the airflow increases rapidly in the upward direction.

The cone and the vaporizing jacket (7) disposed around it together define a narrow conical gap, as described above. The conical gap has an upper end in the vicinity of the upper end of the passage defined by the cone and a lower end in communication with the bottom of the reservoir (12) defined within the lower vaporizing chamber (6).

As the airflow exits from within, and at the apex of, the cone at a very high speed, a negative pressure is created around the apex. As the upper end of the conical gap is open around the apex and by reason of the negative pressure created there, the liquid medication in the reservoir (12) is sucked into the conical gap from the lower end of the gap and travels upwards along the gap.

The liquid medication is subsequently atomized or vaporized by the high-speed airflow, upon exit from the upper end of the conical gap or the vaporizing cap (8) of the vaporizing jacket (7). The vaporized liquid medication is accumulated within the upper vaporizing chamber (9) and ejected out from the air outlet (13) for inhaling by the user.

As the interior of the vaporizing chamber (9 and 6) is in communication with the ambient atmosphere via the opening through the air inlet (22) of the lid (21) and the orifice of the upper vaporizing chamber (9), air will be drawn in through the opening as a result of the inhaling action of the user. The size of the opening may be adjusted by turning the disc (20) or its cut-out, whereby the amount of the intake air and in turn the concentration of vaporized medication to be inhaled may be adjusted.

The subject hand-held compressor nebulizer may be equipped with a mouthpiece and a mask for the user to choose for use as necessary. Also, a battery charger, which may be operated on the mains power supply or a 12V car battery, may be included or supplied for recharging the internal battery of the nebulizer.

Due to the employment of a small electric motor and a small size air pump and the compact design of the vaporizing unit and the liquid medication supply unit, the subject nebulizer may be miniaturized to a size suitable for portable use. In particular, the subject nebulizer is made to have a maximum size of 7 cm×6 cm×23 cm and to weigh at most 750 grams.

The invention has been given by way of example only, and various modifications of and/or alterations to the described embodiment may be made by persons skilled in the art without departing from the scope of the invention as specified in the appended claims.

What is claimed is:

1. A hand-held compressor nebulizer comprising:
   a casing containing an air pump, an electric motor for driving the air pump, and an electrical switch for controlling operation of the motor;
   a liquid medication supply unit located on an upper part of the casing for supplying a liquid medication;
   a vaporizing unit located on the upper part of the casing and comprising an upper vaporizing chamber;
   a lower vaporizing chamber including a reservoir into which the liquid medication supply unit is to supply the liquid medication;
   a hollow conical member located within the lower vaporizing chamber and defining an internal conical passage having a relatively smaller upper end and a relatively larger lower end, the lower end being in communication with the air pump for receiving an upward airflow produced by the air pump, the upward airflow increasing in speed upwardly and creating a negative pressure upon exit from the upper end of the conical passage; and
   a vaporizing jacket having a tapered interior, disposed around the conical member, and forming a narrow gap between the jacket and the conical member, the gap having an upper end proximate the upper end of the conical passage and a lower end in communication with the reservoir, wherein the negative pressure causes the liquid medication in the reservoir to move upward along the gap and to be vaporized by the airflow upon exit from the upper end of the gap, wherein the liquid medication supply unit comprises a holder for holding a liquid medication box closed by a sealing tape, and a slider for piercing the sealing tape to allow the liquid medication in the medication box to flow out into the reservoir.

2. The hand-held compressor nebulizer as claimed in claim 1, wherein the upper vaporizing chamber is formed within the vaporizing unit and the lower vaporizing chamber is defined by a member extending across an uppermost end of the casing.

3. The hand-held compressor nebulizer as claimed in claim 1, wherein the holder is located on the upper vaporizing chamber, the slider and the medication box are arranged on opposite sides within the holder, and wherein the slider is resiliently biased away from the medication box by means of a spring and is movable against the action of the spring to pierce through the tape.

4. The hand-held compressor nebulizer as claimed in claim 1, wherein the air pump is one of a valve-type pump and a plunger-type pump.

5. The hand-held compressor nebulizer as claimed in claim 1, wherein the motor has a power rating of substantially 18 watts.

6. The hand-held compressor nebulizer as claimed in claim 1, wherein the sealing tape is made of one of paper and tin foil.

7. The hand-held compressor nebulizer as claimed in claim 1, wherein the compressor nebulizer has a maximum size of 7 cm×6 cm×23 cm.

8. The hand-held compressor nebulizer as claimed in claim 1, wherein the compressor nebulizer has a maximum weight of 750 grams.

9. The hand-held compressor nebulizer as claimed in claim 1, wherein the upper and lower ends of the conical passage defined by the conical member are substantially 0.7 mm and 3.0 mm in diameter, respectively.

10. The hand-held compressor nebulizer as claimed in claim 1, wherein the gap between the jacket and the conical member is conical and has a gap width of substantially 0.5 mm.

11. A hand-held compressor nebulizer comprising:
   a casing comprising an air pump, an electric motor for driving the air pump, and an electrical switch for controlling operation of the motor;
   a liquid medication supply unit located on an upper part of the casing for supplying liquid medication:
   a vaporizing unit located on the upper part of the casing and comprising an upper vaporizing chamber;
   a lower vaporizing chamber including a reservoir into which the liquid medication supply unit is to supply the liquid medication;
   a hollow conical member located within the lower vaporizing chamber and defining an internal conical passage having a relatively smaller upper end and a relatively larger lower end, the lower end being in communication with the air pump for receiving an upward airflow produced by the air pump, the upward airflow increasing in speed upwardly and creating a negative pressure upon exit from the upper end of the conical passage; and
   a vaporizing jacket having a tapered interior, disposed around the conical member, and forming a narrow gap between the jacket and the conical member, the gap having an upper end proximate the upper end of the conical passage and a lower end in communication with the reservoir, wherein the negative pressure causes the liquid medication in the reservoir to move upward along the gap and to be vaporized by the upward airflow upon exit from the upper end of the gap and wherein the vaporizing unit further comprises a lid having an air inlet above the upper vaporizing chamber for communication of the upper vaporizing chamber with the ambient atmosphere, and an adjuster located immediately below the lid for movement to adjust opening size of the air inlet.

12. The hand-held compressor nebulizer as claimed in claim 11, wherein the upper vaporizing chamber is within the vaporizing unit and the lower vaporizing chamber is defined by a member extending across an uppermost end of the casing.

13. The hand-held compressor nebulizer as claimed in claim 11, wherein the air pump is one of a valve-type pump and a plunger-type pump.

14. The hand-held compressor nebulizers claimed in claim 11, wherein the motor has a power rating of substantially 18 watts.

15. The hand-held compressor nebulizer as claimed in claim 11, wherein the compressor nebulizer has a maximum size of 7 cm×6 cm×23 cm.

16. The hand-held compressor nebulizer as claimed in claim 11, wherein the compressor nebulizer has a maximum weight of 750 grams.

17. The hand-held compressor nebulizer as claimed in claim 11 wherein the upper and lower ends of the conical passage defined by the conical member are substantially 0.7 mm and 3.0 mm in diameter, respectively.

18. The hand-held compressor nebulizer as claimed in claim 11, wherein the gap between the jacket and the conical member is conical and has a gap width of substantially 0.5 mm.

* * * * *